(12) United States Patent
Nique et al.

(10) Patent No.: US 7,449,572 B2
(45) Date of Patent: Nov. 11, 2008

(54) PROCESS AND INTERMEDIATES FOR PREPARING 17-HALOGENATED 19-NORSTEROID COMPOUNDS

(75) Inventors: Francois Nique, Le Perreux (FR); Christian Moratille, Bry sur Marne (FR); Patrick Roussel, Thiais (FR); Joëlle Bousquet, Lyons (FR)

(73) Assignee: Aventis Pharma S.A., Antony, Cedex (FR)

( * ) Notice: Subject to any disclaimer, the term of this patent is extended or adjusted under 35 U.S.C. 154(b) by 838 days.

(21) Appl. No.: 10/834,638

(22) Filed: Apr. 29, 2004

(65) Prior Publication Data

US 2004/0224933 A1    Nov. 11, 2004

(30) Foreign Application Priority Data

Apr. 29, 2003    (FR) .................................. 03 05222

(51) Int. Cl.
*C07J 43/00* (2006.01)
*C07J 1/00* (2006.01)
(52) U.S. Cl. ...................... 540/113; 552/502
(58) Field of Classification Search ............... 540/76; 552/502

See application file for complete search history.

(56) References Cited

U.S. PATENT DOCUMENTS 3,275,623 A    9/1966    Knox et al.

FOREIGN PATENT DOCUMENTS

| FR | 2640977 | 12/1988 |
| WO | WO9925725 | 5/1999 |
| WO | WO 99/67274 | * 12/1999 |
| WO | WO9967274 | 12/1999 |

* cited by examiner

*Primary Examiner*—Barbara P Badio
(74) *Attorney, Agent, or Firm*—Harness, Dickey & Pierce, P.L.C.

(57) ABSTRACT

The invention relates to a process for preparing compounds of formula (I):

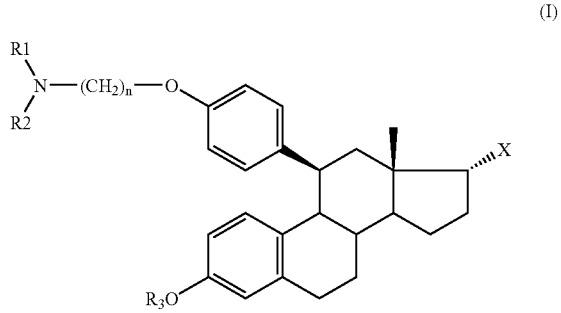

(I)

in which $R_1$, $R_2$, $R_3$, n and X are as defined in the description, and to the intermediate compounds for implementing this process.

19 Claims, No Drawings

PROCESS AND INTERMEDIATES FOR PREPARING 17-HALOGENATED 19-NORSTEROID COMPOUNDS

This application claims the benefit of priority of French Patent Application No. 03/05,222, filed Apr. 29, 2003.

BACKGROUND OF THE INVENTION

1. Field of the Invention

The present invention relates to a process for preparing estrogen derivatives, such as 17-halogenated 19-norsteroids, and also to the intermediate compounds prepared during the implementation of this process.

2. Description of the Art

Osteoporosis is a bone disease which affects 50 million individuals throughout the world, more particularly women. Its development is age-related and most commonly begins after the menopause. This disease is characterized by a decrease in bone density, and results in deformations, vertebral compression and, ultimately, spontaneous fractures. Osteoporosis therefore represents a serious risk to public health. The main treatment consists in regularly taking estrogens, which decreases the bone loss but which, however, can be accompanied by certain side effects (bleeding, hot flushes, risk of breast cancer, etc.). A new series of molecules, called SERMs (Selective Estrogen Receptor Modulators), enables the treatment of osteoporosis while at the same time avoiding some of the side effects.

Patent application WO 99/67274 describes molecules having a 19-norsteroid structure, which are halogenated in the 17-position. Also, disclosed therein is a process of preparation of these compounds involving the halogenation at the end of the synthesis. The synthesis has now been optimized in the present invention:
- by reducing the number of steps with the steroid substrate;
- by carrying out the halogenation right at the beginning of the synthesis in order to make the purification easier.

All of the references described herein are incorporated herein by reference in their entirety.

SUMMARY OF THE INVENTION

Accordingly, the subject of the present application is the development of a novel process for preparing a key intermediate or finished product (compound of formula I) in the synthesis of some of these estrogen derivatives having dissociated activity.

A subject of the invention is a process for preparing compounds of formula (I):

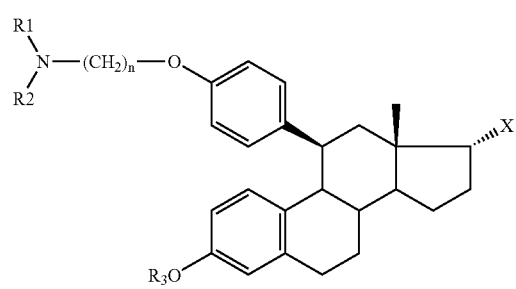

in which
either $R_1$ and $R_2$, which may be identical or different, represent a benzyl group or a linear, branched or cyclic alkyl, alkenyl or alkynyl radical containing from 1 to 8 carbon atoms,
or $R_1$ and $R_2$ taken together with the nitrogen atom to which they are attached form a saturated or unsaturated, aromatic or nonaromatic 5- or 6-membered heterocycle optionally containing from 1 to 3 additional hetero atoms and optionally joined to another ring,
X represents a halogen atom,
$R_3$ represents a hydrogen atom or a hydroxyl function-protecting group,
n is an integer from 2 to 8,
comprising the following steps:
a) a compound of formula (II):

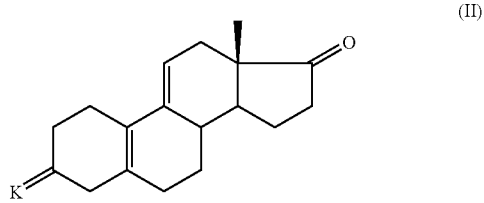

=K representing a protected keto function in particular in the form of a ketal, thioketal or a mixed ketal,
is subjected to the action of an agent for reducing the keto in the 17-position in order to obtain a compound of formula (III):

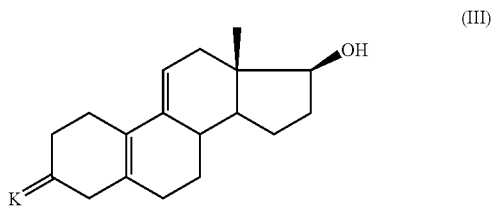

b) the compound of formula (III) is treated with a halogenating agent in order to obtain a compound of formula (IV):

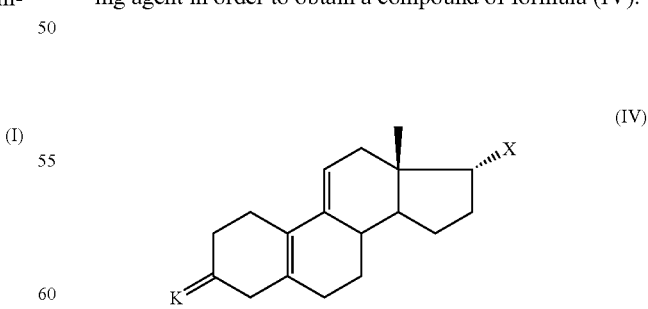

in which X represents a halogen atom,
c) the compound of formula (IV) is subjected to the action of an epoxidation reagent in order to obtain the compound of formula (V):

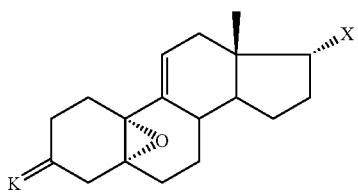

(V)

d) the compound of formula (V) is subjected to an alkylation reaction with an organocuprate derivative derived from an organometallic compound of formula $R_5MgHal$ or $R_5Li$, Hal being a halogen atom, and generated catalytically or stoichiometrically, in which $R_5$ represents the group:

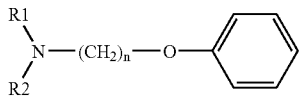

n, $R_1$ and $R_2$ being as defined above, the bonding taking place at the level of the phenyl, and then to the action of a deprotecting agent in order to obtain the compound of formula (VI):

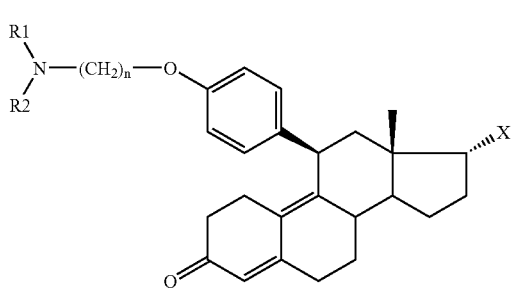

(VI)

e) the compound of formula (VI) is treated with an aromatization agent in order to obtain the compound of formula (I), f) where appropriate, the product obtained in stage e is deprotected in order to obtain a compound of formula (I) in which $R_3$ represents a hydrogen atom, which is subjected, where appropriate, to neutralization and to salification.

As an example of a linear or branched alkyl radical containing from 1 to 8 carbon atoms, mention may be made of methyl, ethyl, propyl, butyl, pentyl, hexyl and octyl radicals, and the branched isomers of these radicals, isopropyl, isobutyl, isopentyl, neopentyl, isohexyl, 3-methylpentyl, sec-butyl, tert-butyl and tert-pentyl.

As an example of a cyclic alkyl radical, mention may be made of the cyclopropyl, cyclobutyl, cyclopentyl and cyclohexyl radicals, and the cycloheptyl or cyclooctyl radicals, which may be substituted, for example, with an alkyl group containing from 1 to 4 carbon atoms.

As an example of an alkenyl radical, mention may be made of the allyl, butenyl or 3-methyl-2-butenyl radicals. As an example of alkynyl radicals, mention may be made of the propargyl radical. Of course, these alkenyl or alkynyl radicals contain at least 2 carbon atoms and are linked to the nitrogen atom via a group $-CH_2-$.

As an example of a heterocycle which may be formed by $R_1$ and $R_2$ taken together with the nitrogen atom to which they are linked, mention may in particular be made of monocyclic or bicyclic heterocycles optionally containing another hetero atom chosen from oxygen and nitrogen, such as the following unsaturated heterocycles: pyrrolyl, imidazolyl, indolyl, pyridyl, pyrazinyl, pyrimidinyl, pyridazinyl, thiazolyl, oxazolyl, furazolinyl, pyrazolinyl; or such as the following saturated heterocycles: morpholinyl, pyrrolidinyl, piperidinyl, oxazolidinyl, thiazolidinyl.

It will preferably be the group:

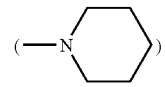

As an example of a halogen atom which may be represented by Hal, mention may be made of chlorine, iodide or bromine. Hal is preferably a bromine atom.

As an example of a halogen atom which may be represented by X, mention may be made of chlorine, bromine, iodine or fluorine. It is preferably fluorine.

As an example of a protective group which may be represented by $R_3$, mention may in particular be made of a group $(C_1-C_6)$ alkyl, $(C_1-C_6)$ alkyl-CO— such as $CH_3CO$ or benzoyl, benzyl, phenyl $(C_1-C_6)$ alkyl such as benzyl, and also all the protective groups known to those skilled in the art, for example those described in Greene, Wuts, Protective Groups in Organic Synthesis 3rd edition, Wiley & Sons, 1999. Preferably, $R_3$, as a protective group, is an acyl group.

As an example of a group for protecting the keto in the 3-position of the steroid, which may be represented by $=K$, mention may in particular be made of the cyclic ketals such as $-O-(CH_2)_m-O-$, $-O-(CH_2)_m-S-$, $-S-(CH_2)_m-S-$, $-O-CH_2-C(C_{1-4}\text{-alkyl})_2-CH_2-O-$, the acyclic ketals such as $(CH_3O)_2$, $(EtO)_2$, and also all the keto group-protecting groups known to those skilled in the art, for example those described in Greene, Wuts, Protective Groups in Organic Synthesis 3rd edition, Wiley & Sons, 1999.

A subject of the invention is more particularly a process as defined above, characterized in that $=K$ is a cyclic ketal, and in particular 3,3-ethylenedioxy.

A subject of the invention is more particularly a process as defined above, characterized in that X represents a fluorine atom.

A subject of the invention is more particularly a process as defined above, characterized in that $R_1$ and $R_2$ form, together with the nitrogen atom to which they are attached, a group

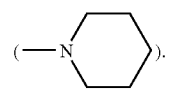

and n is equal to 2.

The reduction of the 17-keto to alcohol is carried out according to conventional methods, in particular by the action of an alkali metal borohydride, such as sodium borohydride, in methanol or ethanol, or by the action of aluminum lithium hydride in THF. This reaction makes it possible in particular to obtain the alcohol in the 17-beta-position. The reduction of the 17-keto to alcohol is preferably carried out by the action of sodium borohydride in methanol.

The halogenation reaction which follows is carried out in particular with reagents such as $XSO_2C_4F_9$ in the presence of a hindered base such as DBU (diazabicycloundecene), X is preferably fluorine. Other methods known to those skilled in the art can also be used.

The halogenation reaction can in particular be carried out in the presence of perfluorobutane sulfonyl fluoride, hydrofluoric acid/triethylamine $((HF)_3, TEA)$ complex and DBU.

The epoxidation reaction is a conventional reaction which is carried out according to the methods known to those skilled in the art. It can be carried out in particular in the presence of hexachloroacetone, dichloromethane and hydrogen peroxide.

The alkylation reaction with an organocuprate derivative derived from an organometallic compound of formula $R_5MgHal$ or $R_5Li$, Hal being as defined above, is carried out according to the conventional methods known to those skilled in the art.

The deprotection reaction which makes it possible to obtain a compound of formula (VI) is carried out according to the conventional methods known to those skilled in the art. The deprotecting agent used is in particular an agent enabling acid hydrolysis, such as hydrochloric acid.

The aromatization reaction followed by the saponification reaction is carried out according to the conventional methods as described in European patent 0097572. This aromatization can preferably be carried out in the presence of acetyl bromine and acetic anhydride.

Where appropriate, the deprotection of the acetyl group formed is generally carried out in the presence of a strong base, such as sodium hydroxide or potassium hydroxide, in an alcohol, such as methanol or ethanol.

The salification and neutralization reactions are carried out by the conventional methods known to those skilled in the art. As used herein the term "salification" refers to formation of a salt of the compound of formula (I) by treating it with a suitable acid agent.

A subject of the invention is also a process for preparing the compounds of formula (VI) from the compounds of formula (II), according to the method as defined above.

The compounds of formula (II) are compounds known to or readily accessible to those skilled in the art. In particular, the compounds of formula (II) in which =K is a 3,3-ethylenedioxy group are described in the article V. Crocq et al., Org. Process. Res. Dev. 1997, 1, 2.

A subject of the invention is also, as novel intermediate compounds, the compound of formula (IV) in which =K represents 3,3-ethylenedioxy,
the compound of formula (V) in which =K represents 3,3-ethylenedioxy,
the compound of formula (VI) in which X represents a fluorine atom, n is equal to 2, and $R_1$ and $R_2$ form, together with the nitrogen atom to which they are linked, a group

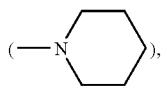

the compound of formula (I) in which $R_3$ represents an acyl group, X represents a fluorine atom, n is equal to 2, and $R_1$ and $R_2$ form, together with the nitrogen atom to which they are linked, a group

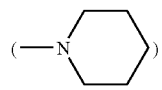

as defined above.

A subject of the invention is more particularly, as novel intermediate compounds,
the compound of formula (IV) in which =K represents 3,3-ethylenedioxy, and X represents a fluorine atom, and
the compound of formula (V) in which =K represents 3,3-ethylenedioxy, and X represents a fluorine atom.

EXPERIMENTAL SECTION

Example 1

11-beta-(4-(2-(1-piperidinyl)ethoxy)phenyl)-17-alpha-fluoroestra-1,3,5(10)-trien-3-ol Stage a: Reduction 3,3-ethylenedioxyestra-5(10), 9(11)-dien-17-ol

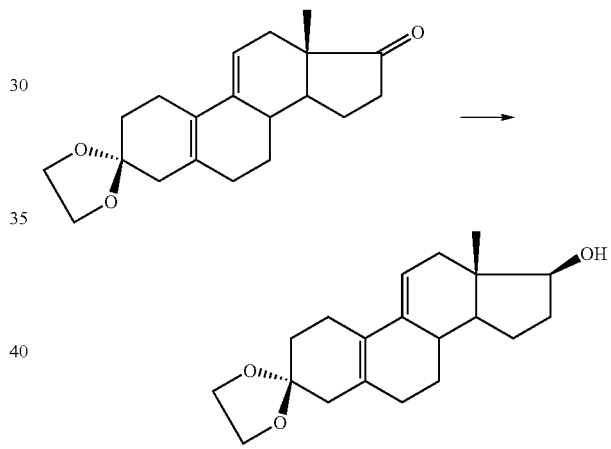

Sodium borohydride (MW=37.8; 18.9 g; 500 mmol) in solution in 0.5 N sodium hydroxide (100 ml) is introduced, over approximately 5 min at around 2° C., into a suspension of 3,3-ethylenedioxyestra-5(10), 9(11)-dien-17-one (MW=314.4; 100 g; 318 mmol) in methanol (1 liter). The mixture is stirred for 2 h at around 2° C. and then acetone (100 ml) is introduced over approximately 15 min at around 5° C. The mixture is stirred for 1 h and the medium is run, at around 20° C., into a stirred mixture of water (2 liters), sodium chloride (500 g) and ethyl acetate (400 ml). The mixture is separated by settling out and the aqueous phase is re-extracted with ethyl acetate. The combined organic phases are washed with water, dried over sodium sulfate and concentrated at normal pressure to 500 ml. The distillation is continued while maintaining the volume constant by gradual introduction of 1,2-dimethoxyethane (DME). The temperature at the end of exchange is 83° C. The solution is used as it is in the subsequent stage, but a dry extract results in the expected product (resin). $C_{20}H_{28}O_3$; MW=316.4:

IR $(CHCl_3, cm^{-1})$: ν 3613, 1638. $^1H$ NMR $(CDCl_3, ppm)$: δ 0.74 (s, 3H), 2.29 (bs, 2H), 3.78 (t, J=8.5 Hz, 1H), 3.98 (m, 4H), 5.57 (m, 1H), from 0.85 to 2.6 (m, 16H).

Stage b: Fluorination 3,3-ethylenedioxy-17-alpha-fluoroestra-5(10), 9(11)-diene

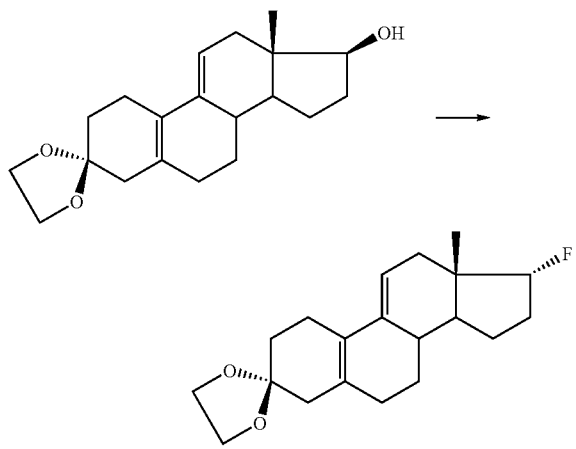

Perfluorobutanesulfonyl fluoride (MW=302.1; 41.4 g; 137 mmol) is introduced, over approximately 5 min at around −10° C., into the solution of 3,3-ethylenedioxyestra-5(10), 9(11)-diene-17-ol (MW=316.4; 20 g; 63.2 mmol) in DME (100 ml) obtained in the preceding stage. The suspension is cooled to around −40° C. and the 3 HF/TEA complex (MW=161.2; 10.2 g; 63.3 mmol) is introduced over approximately 30 min at this temperature. The mixture is stirred for approximately 15 min at about −40° C. and then 1,8-diazabicyclo(5.4.0)undec-7-ene (DBU) (MW=152.2; 38.4 g; 252 mmol) is introduced over approximately one hour at this temperature. The yellow suspension is stirred for 15 min at around −40° C. and then for 3 h at around 2° C. The medium is run into a stirred mixture of water (400 ml), ammonium chloride (80 g) and ethyl acetate (140 ml), at around 10° C. The mixture is stirred for 30 min and separated by settling out, and re-extraction is carried out with ethyl acetate. The combined organic phases are washed with water and with 1N sodium hydroxide, and dried over sodium sulfate. After concentration under vacuum, dichloromethane (300 ml) is introduced. Silica (Merck Si60; 60 g) is introduced into the solution. Stirring is carried out for one hour at around 20° C., the silica is filtered off and rinsed with dichloromethane (80 ml). The filtrate is concentrated up to 80 ml under normal pressure. The distillation is continued while maintaining the volume constant by gradual introduction of isopropanol. The temperature at the end of exchange is 82° C. The solution is returned to around 20° C., crystallization is initiated at around 63° C. The suspension is stirred for one hour at around 20° C. It is spin-filtered at 20° C. and drying is carried out under vacuum overnight at around 40° C. 12.34 g of white product are obtained (yield: 61%) (M.p.=100° C.). $C_{20}H_{27}O_2F$; MW=318.4.

IR (CHCl$_3$, cm$^{-1}$): ν 1640, 1610; $^1$H NMR (CDCl$_3$, ppm): δ 0.66 (d, J=2.5 Hz, 3H), 3.99 (bs, 4H), 4.59 (dd, J=55 and 5 Hz; 1H), 5.60 (m, 1H), from 0.8 to 2.6 (m, 18H); MS (EI; m/z): 318 (M$^+$), 298 (M$^+$−HF).

Stage c: Epoxidation 3,3-ethylenedioxy-17-alpha-fluoro-5(10)-epoxyestr-9(11)-ene

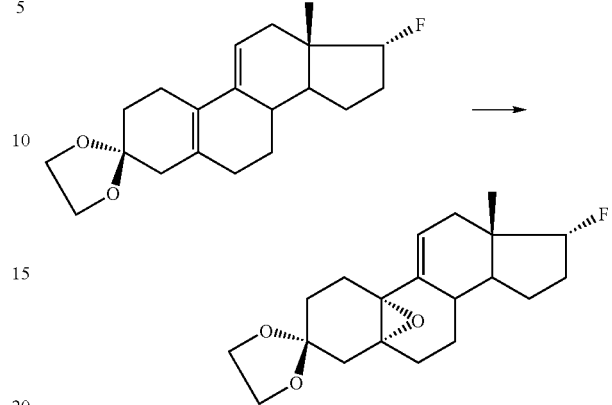

The 3,3-ethylenedioxy-17-alpha-fluoroestra-5(10), 9(11)-diene (100 g; MW: 318.4; 0.314 mol), hexafluoroacetone (trihydrate; 22.3 ml; 0.5 eq.), pyridine (10 ml), 50% hydrogen peroxide (approx. 18 M; 43.5 ml; 2.5 eq.) and dichloromethane (1000 ml) are stirred vigorously for 18 h at 0-5° C. After reduction in the presence of aqueous sodium thiosulfate, washes (water) and extractions (dichloromethane), the organic phase is dried over sodium sulfate. Silica (Merck Si 60, 100 g) is then added, the suspension is stirred for 30 min at around 20° C., and filtration and rinsed with dichloromethane (200 ml). The filtrate is concentrated to 300 ml under vacuum and distillation is carried out at constant volume by introduction of n-heptane (T at the end of exchange: 98° C.). Cooling is performed with stirring, the alpha-epoxide crystallizes at around 55° C. Stirring is performed for 16 h at around 20° C., followed by filtration and drying under vacuum at around 40° C. 53.5 g of white solid are obtained (yield: 51%) (M.p.=115° C.). A second crop of 14 g (i.e. 13%) is recovered by silica chromatography of the mother liquors (eluent: 80/20 heptane/ethyl acetate); $C_{20}H_{27}O_3F$; MW: 334.4:

IR (CHCl$_3$, cm$^{-1}$): ν 1640; $^1$H NMR (CDCl$_3$, ppm): δ 0.66 (d, J=2 Hz, 3H), 3.85 to 3.97 (m, 4H), 4.58 (dd, J=55 and 5 Hz, 1H), 6.07 (dt, J=5.5 and 2.5 Hz, 1H), from 1.15 to 2.57 (m, 18H).

Stage d: Alkylation 17-alpha-fluoro-11-beta-(4-(2-(1-piperidinyl)ethoxy)-phenyl)estra-4,9-diene-3-one.

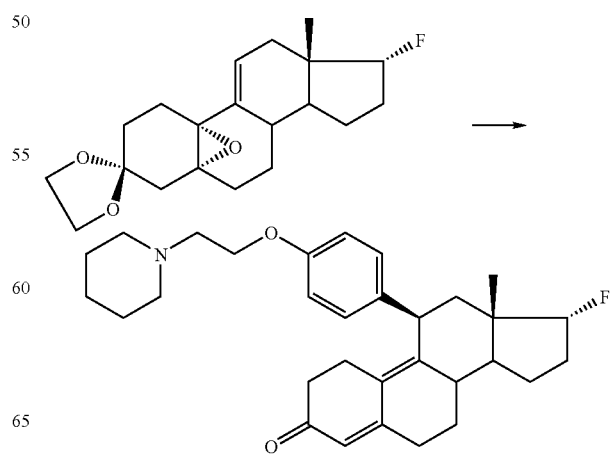

6.7 g of magnesium (turnings; MW=24.3; 1.8 eq.) are introduced into a reactor, followed by 56 ml of a solution of 4-(2-(1-piperidinyl)ethoxy)benzene bromide (70 g; MW=284.2; 1.65 eq.) in THF (280 ml). The mixture is heated at around 58° C. and, as soon as the medium becomes gray, the remainder of the solution is introduced at around 58° C., over approximately 1.5 h, and the mixture is kept at this temperature for a further 2 h. The solution is brought to 20° C. and stirred for 18 h. Cuprous chloride (1.5 g; MW=99.0; 0.1 eq.) is introduced, the mixture is stirred for approximately 5 min at around 20° C., and then a solution of 3,3-ethylenedioxy-17-alpha-fluoro-5(10)-alpha-epoxyestr-9(11)-ene (50 g; MW=334.4; 149 mmol) in THF (200 ml) is introduced over 30 min at around 5° C. Stirring is performed for one hour at around 5° C. and the medium is run into a stirred mixture of ammonium chloride (250 g), water (1 liter) and dichloromethane (500 ml), at around 10° C. The mixture is separated by settling out and the aqueous phase is re-extracted with dichloromethane. The combined organic phases are washed with water and are concentrated to approximately 250 ml under vacuum. The solution is cooled to around 2° C. and water (125 ml) followed by concentrated hydrochloric acid (36%; 75 ml) are introduced, still at around 2° C. Stirring is performed for 1.5 h at around 2° C., and the medium is diluted with water (250 ml) and separated by settling out, and washed with water. The medium is run into a stirred mixture of sodium bicarbonate (23.5 g; MW=84.0; 1.9 eq.) in water (250 ml), at around 20° C., over approximately 30 min (foam formation). The mixture is stirred for 30 min and separated by settling out. The aqueous phases are re-extracted with dichloromethane, washed with water and dried over sodium sulfate. Then, the mixture is filtered and rinsed with dichloromethane. The filtrate is concentrated to approximately 250 ml at normal pressure and the distillation is then continued while maintaining the volume constant by gradual introduction of isopropyl ether. The temperature at the end of exchange is 68° C. Crystallization is spontaneous. The mixture is allowed to cool to around 20° C. and stirred for a further period of 2 h at around 20° C. Spin-filtering and drying under vacuum at around 40° C. afforded 56.1 g of beige solid (yield: 78%) (M.p.=160° C.): $C_{31}H_{40}FNO_2$; MW: 477.7;

IR ($CHCl_3$, $cm^{-1}$): 1656, 1608, 1508; $^1$H NMR ($CDCl_3$, ppm): 0.35 (d, J=2 Hz, 3H); 1.44 (m, 2H); 1.60 (m, 4H); 2.50 (bl, J=6 Hz, 4H); 2.76 (t, 6 Hz, 2H); 4.07 (t, 6 Hz, 2H); 4.39 (m, 1H); 4.46 (dd, J=55.5 and 5 Hz, 1H); 5.76 (bs, 1H); 6.82 and 7.07 (AA'BB', 4H); from 1.2 to 4.1 (m, 18H); MS (EI ; m/z): 477 ($M^+$); 457 ($M^+$–HF); 366; 346; 98.

Stage e: Aromatization 3-acetyloxy-11-beta-(4-(2-(1-piperidinyl)ethoxy)phenyl)-17-alpha-fluoroestra-1,3,5(10)-triene.

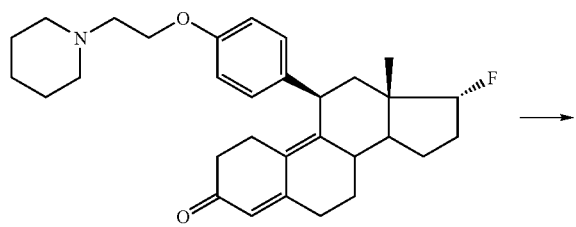

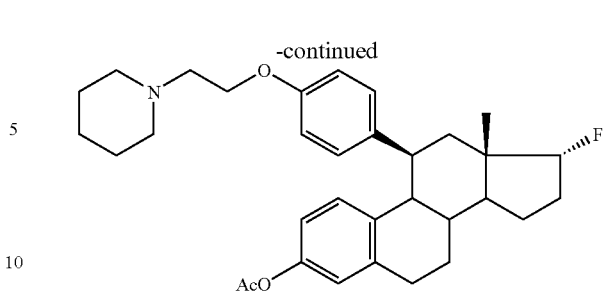

Acetic anhydride (MW=102.1; d =1.09; 7.5 ml; 1.0 eq.) and, over 15 min, acetyl bromide (MW=123.0; d=1.66; 14.7 ml; 2.5 eq.) are added to a solution of 17-alpha-fluoro-11-beta-(4-(2-(1-piperidinyl)ethoxy)phenyl)-estra-4,9-diene-3-one (38 g; MW=477.7; 79.5 mmol) (stage d) in dichloromethane (152 ml), at 20-25° C. (exothermic addition). The brown solution is stirred for 5 h at 20-25° C. The solution is poured, over approximately 30 min, into a suspension of sodium hydrogen carbonate (45 g) in water (380 ml) at around 20° C. (carbon dioxide given off). The mixture is stirred vigorously overnight at around 20° C., and the organic phase is then separated by settling out, washed with 1 N sodium hydroxide (190 ml) and water, and concentrated to a final volume of 114 ml. The dichloromethane is replaced with methanol at constant volume by distillation under gradual vacuum at approximately 40° C. The product is stored in solution in methanol. $C_{33}H_{42}FNO_3$; MW: 519.8.

Stage f: Saponification 11-beta-(4-(2-(1-piperidinyl)ethoxy)phenyl)-17-alpha-fluoroestra-1,3,5(10)-trien-3-ol hydrochloride

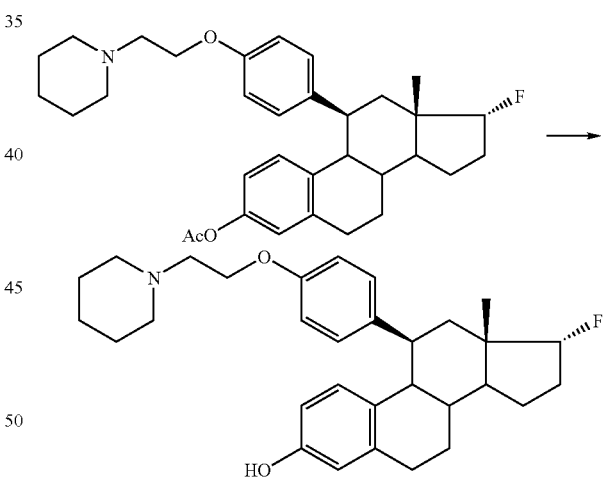

A solution of potassium hydroxide (MW=56.0; 6.7 g; 1.5 eq.) in methanol (76 ml) is added to the solution of the fluorinated derivative in methanol, obtained in stage e, over approximately 10 min at around 0° C. The medium is stirred for 45 min at 0-5° C., and then poured into water (190 ml) and dichloromethane (190 ml). The organic phase is washed with water. Acidification is carried out by adding methanol (76 ml), water (190 ml) and 36% hydrochloric acid (17 ml; 2.5 eq.) and stirring is performed for approximately 5 min. verifying the pH (<2). The organic phase is separated by settling out, dried over sodium sulfate, filtered and concentrated until a final volume of 190 ml is obtained. Distillation is then performed at normal pressure while maintaining the volume constant by gradual introduction of dichloromethane (approximately 450 ml). The expected product crystallizes spontaneously. The product is stirred while being allowed to cool over approximately 1 h, and then for 2 h at around 20° C. The product is filtered, washed with dichloromethane and then dried under vacuum at around 40° C. 30.8 g of beige solid are obtained (yield: 75.3%); HPLC purity: 98%): $C_{31}H_{41}ClFNO_2$; MW: 514.1;

IR (CHCl$_3$, cm$^{-1}$): ν=3599; 2467; 1609; 1583; 1511. $^1$H NMR (CDCl$_3$, ppm): 0.22 (d, J=1.5 Hz, 3H); 3.09 (m, 1H); 3.21 (m, 1H); 3.87 (m, 1H); 3.99 (m, 1H); 4.25 (m, 1H); 4.43 (dd, J=56 and 5 Hz, 1H); 6.43 and 6.95 (AA'BB', 4H); 6.60 (dd, J=8.5 and 1.5 Hz, 1H); 6.67 (d, J=1.5 Hz, 1H); 6.78 (d, J=8.5 Hz, 1H); 11.4 (bs, 1H mobile); from 0.9 to 3.4 (m, 14H). MS (ESP; m/z): 478 (MH$^+$).

Stage g: Neutralization 11-beta-(4-(2-(1-piperidinyl)ethoxy)phenyl)-17-alpha-fluoroestra-1,3,5(10)-trien-3-ol Sodium carbonate (MW=106.0; 6.1 g; 1 eq.) in aqueous solution (112 ml) is introduced, at around 20° C., into a suspension of 11-beta-(4-(2-(1-piperidinyl)ethoxy)-phenyl)-17-alpha-fluoroestra-1,3,5(10)-trien-3-ol hydrochloride (28 g; MW=514.1; 54.5 mmol) (stage f) in dichloromethane (224 ml). The mixture is stirred for 30 min at around 20° C., separated by settling out and washed with water. The organic phase is dried over sodium sulfate and filtered, and the filtrate is concentrated to a residual volume of 140 ml. It is returned to 20° C. and acetone (280 ml) is introduced, followed by silica (Merck Si 60; 42 g). The mixture is stirred for one hour at around 20° C., filtered and rinsed with a 2/1 acetone/dichloromethane mixture. The filtrate is concentrated until a final volume of 224 ml is obtained. Distillation is then carried out at normal pressure, while maintaining the volume constant by gradual introduction of isopropanol. The product crystallizes spontaneously. The product is stirred while being allowed to cool over approximately 1 h, and then for 2 h at around 0° C. The product is filtered off, washed with isopropanol at around 0° C. and then dried under vacuum at around 40° C. 21.3 g of white solid are obtained (yield: 82.1%; HPLC purity: 99%; M.p.=180° C.): $C_{31}H_{40}FNO_2$; MW: 477.7;

IR (CHCl$_3$, cm$^{-1}$): ν=3598, 1610, 1581, 1512; $^1$H NMR (CDCl$_3$, ppm): 0.16 (d, J=2.5 Hz, 3H); 1.34 (m, 2H); 1.44 (m, 4H); 2.37 (m, 4H); 2.56 (t, J=6 Hz, 2H); 3.91 (m, 2H); 3.95 (m, 1H); 4.44 (dd, J=56 and 5 Hz, 1H); 6.31 (dd, J=8.5 and 3 Hz, 1H); 6.46 (d, J=3 Hz, 1H); 6.63 and 6.97 (AA'BB', 4H); 6.71 (d, J=8.5 Hz, 1H); 8.95 (bs, 1H mobile); from 0.9 to 3.0 (m, 13H).

What is claimed is:

1. A process for preparing compounds of formula (I):

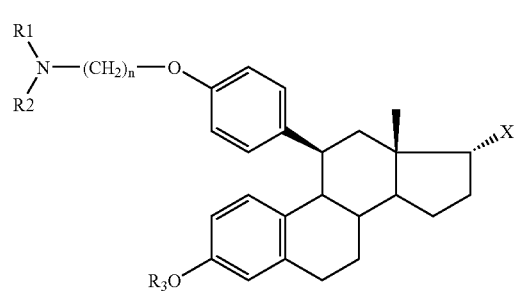

wherein

R$_1$ and R$_2$, which may be identical or different, represent a benzyl group or a linear, branched or cyclic alkyl, alkenyl or alkynyl radical containing from 1 to 8 carbon atoms; or R$_1$ and R$_2$, taken together with the nitrogen atom to which they are attached form a saturated or unsaturated, aromatic or nonaromatic 5- or 6-membered heterocycle optionally containing from 1 to 3 additional heteroatoms and optionally fused with another ring;

X is halogen;

R$_3$ is hydrogen or a hydroxyl function-protecting group;

n is an integer from 2 to 8, comprising the steps of:

a) subjecting a compound of formula (II):

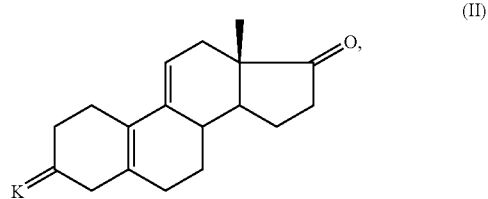

wherein =K is a protected keto functional group selected from ketal, thioketal or a mixed ketal, to the action of an agent for reducing the keto in the 17-position in order to obtain a compound of formula (III):

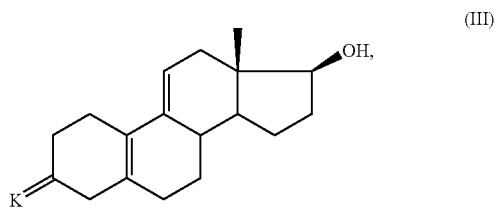

b) treating the compound of formula (III) with a halogenating agent in order to obtain a compound of formula (IV):

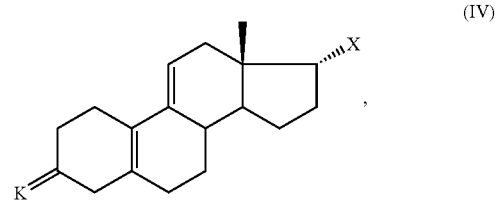

wherein X is halogen;

c) subjecting the compound of formula (IV) to the action of an epoxidation reagent in order to obtain the compound of formula (V):

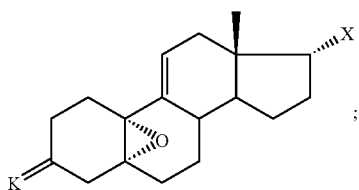 (V)

d) subjecting the compound of formula (V) to an alkylation reaction with an organocuprate derivative derived from an organometallic compound of formula $R_5MgHal$ or $R_5Li$, Hal being a halogen atom, and generated catalytically or stoichiometrically, wherein $R_5$ is:

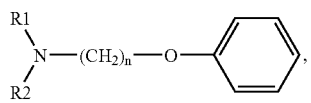

wherein n, $R_1$ and $R_2$ are as defined above, the bonding taking place at the level of the phenyl, and then to the action of a deprotecting agent in order to obtain the compound of formula (VI):

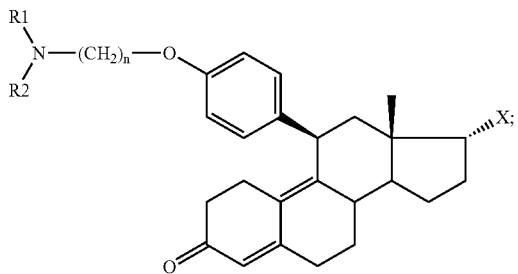 (VI)

e) treating the compound of formula (VI) with an aromatization agent in order to obtain the compound of formula (I);

f) deprotecting, optionally, the product obtained in stage e to obtain a compound of formula (I), wherein $R_3$ is hydrogen, and optionally, converting it into a pharmaceutically acceptable salt by subjecting it to a suitable salification and neutralization reaction.

2. The process as set forth in claim 1, wherein =K is a cyclic ketal.

3. The process as set forth in claim 2, wherein =K is 3,3-ethylenedioxy.

4. The process as set forth in claim 1, wherein X is fluorine.

5. The process as set forth in claim 2, wherein X is fluorine.

6. The process as set forth in claim 1, wherein $R_1$ and $R_2$ taken together with the nitrogen atom to which they are attached form a group

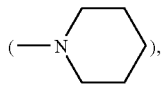

and n is equal to 2.

7. The process as set forth in claim 1, wherein the reduction of the 17-keto to alcohol is carried out by the action of sodium borohydride in methanol.

8. The process as set forth in claim 1, wherein the halogenation reaction is carried out with perfluorobutanesulfonyl fluoride in the presence of a hydrofluoric acid/triethylamine complex and diazabicycloundecene.

9. The process as set forth in claim 1, wherein the deprotecting agent used to obtain the compound of formula (VI) is an agent enabling acid hydrolysis.

10. The process as set forth in claim 9, wherein the agent enabling acid hydrolysis is hydrochloric acid.

11. The process as set forth in claim 1, wherein the aromatization reaction is carried out in the presence of acetyl bromide and of acetic anhydride.

12. The process as set forth in claim 1, wherein step d) obtains a compound of formula (VI), wherein X is fluorine, n is equal to 2, and $R_1$ and $R_2$ taken together with the nitrogen atom to which they are attached form a group

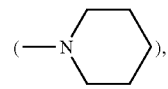

13. The process as set forth in claim 1, wherein steps a) through f) prepare a compound of formula (I), wherein $R_3$ is an acyl group, X is fluorine, n is equal to 2, and $R_1$ and $R_2$ taken together with the nitrogen atom to which they are attached form a group

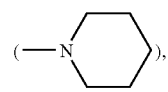

14. A process for preparing the compounds of formula (IV):

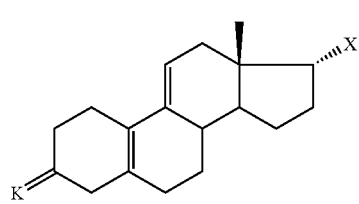 (IV)

wherein X is halogen,
comprising the steps of:
a) subjecting a compound of formula (II):

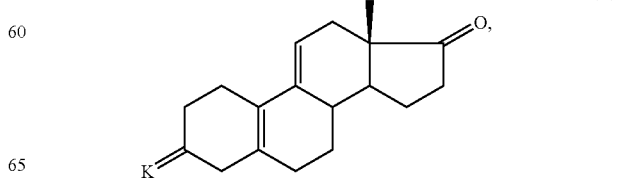 (II)

wherein =K is a protected keto functional group selected from ketal, thioketal or a mixed ketal, to the action of an agent for reducing the keto in the 17-position in order to obtain a compound of formula (III):

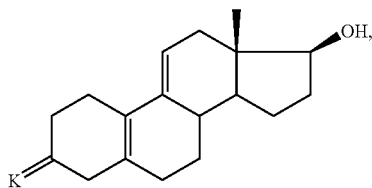

(III)

b) treating the compound of formula (III) with a halogenating agent in order to obtain a compound of formula (IV).

15. A compound of formula (IV):

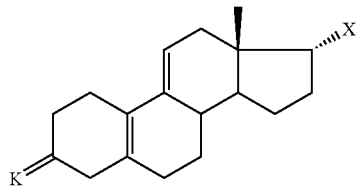

(IV)

wherein =K is cyclic ketal; and X is halogen.

16. The compound as set forth in claim 15 wherein =K is 3,3-ethylenedioxy; and X is fluorine.

17. A compound of formula (V):

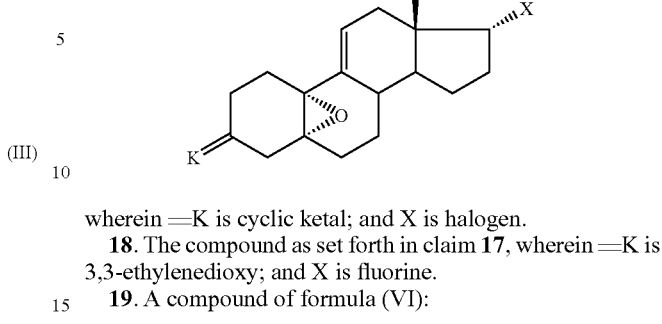

(V)

wherein =K is cyclic ketal; and X is halogen.

18. The compound as set forth in claim 17, wherein =K is 3,3-ethylenedioxy; and X is fluorine.

19. A compound of formula (VI):

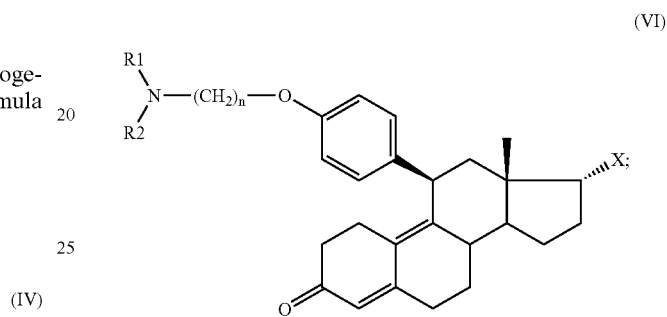

(VI)

wherein X is fluorine, n is equal to 2, and $R_1$, and $R_2$ taken together with the nitrogen atom to which they are attached form a group

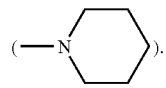

* * * * *